United States Patent [19]

Griffith

[11] 4,042,337

[45] Aug. 16, 1977

[54] URINE COLLECTION DEVICE

[76] Inventor: Donald P. Griffith, 1200 Moursund, Houston, Tex. 77025

[21] Appl. No.: 769,693

[22] Filed: Feb. 17, 1977

[51] Int. Cl.$^2$ .................. G01N 33/16; G01N 1/10; A61B 10/00

[52] U.S. Cl. .................................. 23/259; 23/253 R; 23/292; 128/2 F

[58] Field of Search ............... 23/259, 253 R, 292, 23/230 B; 128/2 F, 295; 73/421 R

[56] References Cited

U.S. PATENT DOCUMENTS

| 3,774,455 | 11/1973 | Seidler et al. | 23/259 |
| 3,781,922 | 1/1974 | Ericson | 128/2 F |
| 3,859,671 | 1/1975 | Tomasello | 23/259 UX |
| 3,894,845 | 7/1975 | McDonald | 23/259 X |
| 3,982,898 | 7/1975 | McDonald | 23/259 X |

Primary Examiner—R.E. Serwin

Attorney, Agent, or Firm—Arnold, White & Durkee

[57] ABSTRACT

A urine collection device is disclosed for use in metabolic studies in which an integrated specimen is desired. The collection device has a receptacle divided into bin sections. A removable manifold cover adapted to fit onto the receptable portion has openings which are arranged to be in registration with a separate one of the bin sections. Urine poured into the manifold will be metered through the openings into the bin sections, with a substantially equal amount entering each. Each bin contains a different chemical substance for preserving some characteristic of the urine. For example, in one bin the urine may be acidified by the substance; in another it may be alkalized; and in another it may have the pH stabilized. The device permits urine samples of a patient to be collected over a period of time, and away from a clinic or hospital without the urine characteristics to be tested changing.

1 Claim, 2 Drawing Figures

URINE COLLECTION DEVICE

BACKGROUND OF THE INVENTION

The present invention relates to a urine collection, preservation, and transportation device for obtaining an integrated urine specimen from a patient over a period of time.

Tests made on the urine of a patient can provide valuable information concerning the bodily condition of a patient, as urine contains waste products of bodily metabolism. Oftentimes in fact an early detection of the metabolic abnormalities which accompany a particular disease will lead to an early cure for the disease. Biochemical studies carried out on urine specimens is an effective way of detecting abnormalities. Since, however, body metabolism is affected by many variables including, for example, dietary excesses or inadequacies, it is often difficult to obtain specimens that are not unduly affected by such factor. To obtain truly representative samples, it is required that patients come into the hospital periodically to give specimens; on some occasions a controlled diet is required. This is of course, time consuming, expensive and inconvenient. Desirably, an integrated specimen taken under normal conditions of activity and diet over a 24 hour period would be preferable; however, heretofore collection of a single integrated specimen for multiple assays has not been possible because different biochemical assays frequently require different techniques of preservation.

SUMMARY OF THE INVENTION

Accordingly, it is a feature of the present invention to provide a urine collection device not only capable of collecting and holding a large volume of liquid urine from a patient, but also capable of deriving an integrated urine specimen over a period of time and preserving several characteristics of the urine's physiological state for prolonged periods, so as to permit accurate biochemical analysis of a multitude of constituents.

For example, urine contains variable quantities of calcium, oxalate, phosphate, and uric acid. Accurate analysis of these constituents necessitates that all remain in solution (i.e., in a dissolved state). At physiologic levels of pH, precipation of calcium oxalate, calcium phosphate or uric acid occurs commonly. Manipulation of the pH will maintain the constituents in solution. However, uric acid requires an alkaline medium to remain in solution and calcium, phosphorus and oxalate require an acid medium to remain in solution. In the past, it has not been possible to collect and preserve a simple, integrated urine specimen for all of these biochemical assays.

The present invention overcomes the problems of multiple assays by providing automatic separation of multiple aliquots of each voided urine specimen so that each aliquot is similar to another in volume and composition. Sequential collection of similar aliquots collected in different bins each containing a different preservative will allow accurate biochemical analysis under similar conditions of collection, but different conditions of preservation.

In accordance with the present invention, a receptacle is divided into bin sections with a removable manifold cover disposed on the receptacle. The manifold has openings therein arranged to be in registration with a separate one of the bins. The manifold further contains an inlet through which urine is poured. Each bin contains a chemical substance for preserving some predetermined condition for the urine.

BRIEF DESCRIPTION OF THE DRAWINGS

For the purpose of more fully explaining other features of the instant invention, a detailed description of a preferred embodiment will be given with reference to the accompanying drawings wherein.

DETAILED DESCRIPTION

Figure 1:
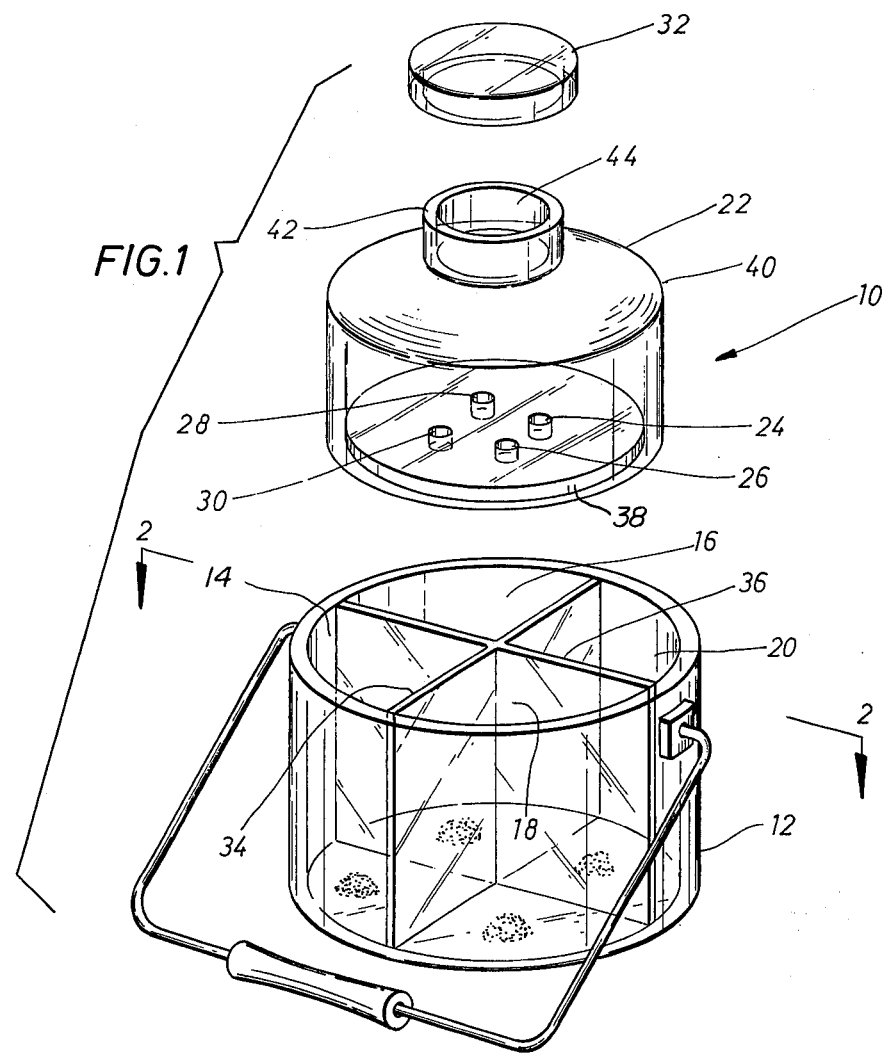
FIG. 1 is a prespective view of one embodiment of a urine collection device in accordance with the present invention.

Referring now to FIG. 1, the urine collection device 10 is shown and will be observed to comprise a receptacle 12 having four bins 14, 16, 18, 20 defined therein. A removable manifold 22 is adapted to fit and be disposed on receptacle 12. Manifold 22 has openings 24, 26, 28, 30, each for registration with a separate one of the bins. An inlet 44 is on the top of manifold 22, into which urine is poured. Urine poured into 44 will be metered through openings 24, 26, 28, 30, with a substantially equal amount entering each bin. A cap 32 will snugly fasten to inlet 44 to fully enclose the apparatus.

In order to preserve the characteristics of the urine collected over time and establish a predetermined condition, a different chemical substance will be present in each bin section. For example, a bin would contain an acidifying substance, or an alkalizing substance, or a substance to stabilize pH and/or substance to prevent bacterial growth and/or a substance to preserve any specific physiologic feature. In particular, sulfamic acid could be placed in one bin to create an acidified liquid urine specimen. In another bin, sodium carbonate could be used to create an alkalinized urine sample. The pH stabilizing substance in another bin could be acetohydroxamic acid and benzyl (dodecylcarbanyl methyl dimethylammonium chloride). Finally, the preservative substance used in the remaining bin could be thymol crystals or any other specific preservative.

Figure 2:
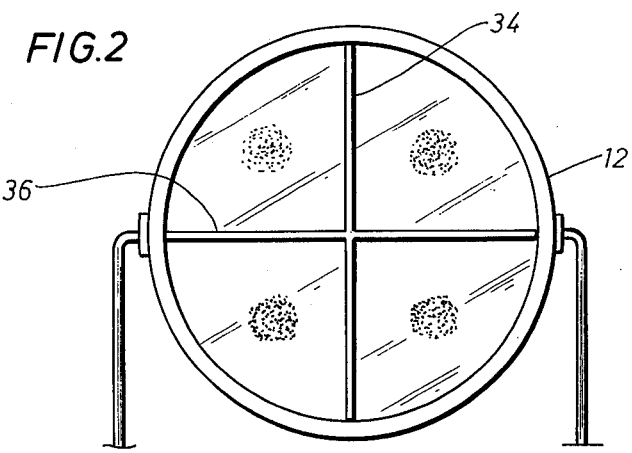
FIG. 2 is a plan view of the device.

As may be seen in FIG. 2, the bins in receptacle 12 are formed by the walls which traverse the diameter of receptacle 12. The receptacle may contain any number of bins of similar size. In the examples illustrated (FIG. 1 and 2) the receptacle is composed of four bins the walls of which intersect at right angles. It is imperative that each bin formed be completely sealed off from the adjacent bins. Therefore, it is desirable that walls 34, 36, be formed integrally with receptacle 12. Accordingly, one desirable manner of producing the urine collection device 10 is by ejection molding of plastic. Of course, other suitable techniques of construction may be utilized and walls 34, 36 may be separately formed. However, some type of seal must be established where the walls 34, 36 and receptacle 12 meet.

Manifold 22 is adapted to fit concentrically onto the top of receptacle 12 and firmly engage it. Manifold 22 may attach to receptacle 12 by threads, permitting the manifold to be screwed onto the receptacle; or manifold 22 may have a snap or clamp mechanism to securely hold it onto receptacle 12. Regardless, however, of how manifold 22 is mounted to receptacle 12, it is necessary that means be provided to assure registration of openings 24, 26, 28, 30 with one of the bins 14, 16, 18, 20. If manifold 22 is screwed onto receptacle 12, proper registration may be achieved by properly placing the openings in manifold 22. One method of placement to provide registration would be to have the openings equally spaced from the center of the receptacle such as ninety degrees apart and disposed a distance away from the center of the manifold. If manifold 22 snaps onto receptacle 12, mating spines and grooves on the two pieces can be used to provide proper alignment.

In addition the same sort of means of attaching it to receptable 12, manifold 22 has a chamber formed between a bottom plate 38, having the openings 24, 26, 28, 30 formed therein, and a top cover 40 which is disposed above plate 38. Urine introduced through inlet 44 is held within the chamber and released at a slow rate through the openings in plate 38.

In use, the device may be given to a patient to take home, with the instructions that urine individual specimens are to be poured into the device through inlet 44 over the prescribed time period, usually 24 hours. The patient returns the device containing an integrated urine specimen after the prescribed period, thereby providing the physician with an integrated urine specimen, containing several nearly identical urine specimens, each preserved differently, on which multiple assays may be run to determine biochemical abnormalities. This procedure is in contrast to that heretofore used wherein a patient would be required to come in on multiple occasions to give separate urine specimens the composition of each of which differed from the other. Such day-to-day differences being a normal biologic variation.

With the urine collection device disclosed herein there is less chance of the urine specimen to be tested being misrepresentative because all biochemical assays will be accurately performed on identical aliquots of the same urine specimen.

The foregoing description of the invention has been directed to a particular preferred embodiment of the present invention for purposes of explanation and illustration. It will be apparent, however, to those skilled in this art that many modifications and changes in the apparatus may be made without departing from the scope and spirit of the invention. It is therefore intended that the following claims cover all equivalent modifications and variations as fall within the scope of the invention as defined by the claims.

What is claimed is:

1. A urine collection device comprising:

a receptacle for holding liquid urine having a bottom and sides,
   said receptacle being divided into separate, non-communicating bins defined by walls extending from the bottom to the upper edge of the sides, one or more of said bins containing a chemical compound for effecting desired characteristics in urine introduced into the respective receptacle bins; and a manifold for attachment atop the sides of said receptacle,
   said manifold including a base plate having at least one opening formed therein for each bin of said receptacle, with each of said openings being positioned to register with a respective one of said bins when said manifold is placed on said receptacle, and
   an upper cover disposed a distance away from said base plate at its center and attached at its periphery to said base plate, said upper cover and said base plate in combination forming a chamber, and
a closeable inlet in the upper end of said manifold communicating with the chamber formed therein for introducing liquid urine into said chamber.

* * * * *